United States Patent [19]

Lee

[11] Patent Number: 5,552,162
[45] Date of Patent: Sep. 3, 1996

[54] METHOD FOR IMPROVEMENT OF SCAR SIZE AND APPEARANCE

[75] Inventor: Raphael C. Lee, Chicago, Ill.

[73] Assignee: Arch Development Corporation, Chicago, Ill.

[21] Appl. No.: 15,216

[22] Filed: Feb. 9, 1993

[51] Int. Cl.$^6$ .................................................. A61K 31/275
[52] U.S. Cl. .................... 424/646; 424/447; 424/445; 424/446; 424/78.02; 514/356; 514/211; 514/648; 514/22.58; 514/649
[58] Field of Search .................................. 424/786, 78.2, 424/646, 447, 445, 446; 514/277, 356, 523, 947, 211, 648, 225.8, 649

[56] References Cited

U.S. PATENT DOCUMENTS

| | | | |
|---|---|---|---|
| 4,272,518 | 6/1981 | Moro et al. | 424/81 |
| 4,659,700 | 4/1987 | Jackson | 514/55 |
| 5,013,769 | 5/1991 | Murray et al. | 523/111 |
| 5,132,119 | 7/1992 | Lee | 424/646 |

FOREIGN PATENT DOCUMENTS

| | | |
|---|---|---|
| WO91/01624 | 2/1991 | WIPO. |
| WO91/02497 | 3/1991 | WIPO. |
| WO91/06323 | 5/1991 | WIPO. |
| WO94/02130 | 2/1994 | WIPO. |

OTHER PUBLICATIONS

Ahn et al., "Topical Silicone Gel for the Prevention and Treatment of Hypertrophic Scar," *Arch Surg.*, 126:499–504, 1991.

Fulton, "The Stimulation of Postdermabrasion Wound Healing with Stabilized Aloe Vera Gel–Polyethylene Oxide Dressing," *J. Dermatol. Surg. Oncol.*, 16(5):460–467, 1990.

Krieger et al.,"Thermal Response of the Epidermis to Surface Cells," 49th Annual Sessions on the forum on Fundamental Surgical Problems, 1993 Clinical Congress, San Francisco, CA, Oct. 10–15, pp. 738–740.

Lee et al., "The Response of Burn Scars to Intralesional Verapamil," *Arch Surg.* 129:107–111, 1994.

Lee and Ping, "Calcium Antagonists Retard Extracellular Matrix Production in Connective Tissue Equivalent," *Journal of Surgical Research*, 49:463–466, 1990.

Ehrlich and Buttle, "Epidermis Promotion of Collagenase in Hypertrophic Scar Organ Culture," *Experimental and Molecular Pathology*, 40:223–234, 1984.

International Search Report dated Jul. 2, 1994.

Ahn et al. (1989) Surgery vol. 106, No. 4, pp. 781–787.

Clinical Comment (1980), vol. 6, No. 3, pp. 1–3.

Jeffrey et al. (1983) The Journal of Biological Chemistry, vol. 258, No. 18, pp. 11123–11127.

Quinn, et al. (1985) Burns 12:102–108.

Quinn, (1987) Burns 13:S33–S40.

Welgus, et al. (1980) The Journal of Biological Chemistry, vol. 256, No. 18, pp. 9511–9515.

Welgus, et al. (1980) The Journal of Biological Chemistry, vol. 256, No. 18, pp. 9516–9521.

*Primary Examiner*—José G. Dees
*Assistant Examiner*—Samuel Barts
*Attorney, Agent, or Firm*—Arnold White & Durkee

[57] ABSTRACT

A method for improving the size and appearance of a scar associated with a fibromatosis, a keloid, or a hypertrophic wound healing disorder comprises stimulating collagenase activity in the scar. Preferably, stimulating collagenase activity is accomplished by covering said scar with a thermal insulating material that elevates the surface temperature of the scar. Further disclosed is a method for improving the size and appearance of a scar comprises covering said scar with a thermal insulating material that elevates the surface temperature of the scar and that contains a therapeutically effective amount of a medicament.

13 Claims, 9 Drawing Sheets

METHOD FOR IMPROVEMENT OF SCAR SIZE AND APPEARANCE

TECHNICAL FIELD OF THE INVENTION

The present invention relates to in general to wound healing and, in particular to a process for improving the size and appearance of scar tissue.

BACKGROUND OF THE INVENTION

Wound Tissue Disorders

The changing patterns of the connective tissue matrix during growth, development, and repair following injury require a delicate balance between synthesis and degradation of collagen and proteoglycans. Under normal circumstances this balance is maintained, while in many diseased states it is altered, leading to an excessive deposition of collagen or to a loss of functional tissue.

Collagen is the major structural constituent of mammalian organisms and makes un a large portion of the total protein content of skin and other parts of the animal body. In humans, it is particularly important in the wound healing process and in the process of natural aging. Various skin traumas such as burns, surgery, infection and accident are often characterized by the erratic accumulation of fibrous tissue rich in collagen and having increased proteoglycan content. In addition to the replacement of the normal tissue which has been damaged or destroyed, excessive and disfiguring deposits of new tissue sometimes form during the healing process.

Although balanced scar formation and remodeling are essential processes in skin wound healing, disorders of excess scar formation remain a common and therapeutically refractory clinical problem. A hypertrophic scar is an excessive wound scar which by definition has grown in size beyond that required for normal wound healing. Hypertrophic scars can emerge from many wound types, such as from a burn or a sharp incision.

Hypertrophic scars generally result from an over-production of cells, collagen and proteoglycan [Linares, H. A. and Larson, D. L., Plast. Reconst. Surg., 62:589 (1978); Linares, H. A., Plast. Reconstr. Surg., 818–820 (1983)]. These scars more frequently occur among children and adolescents, suggesting that growth factors may influence the development of this type of scar. Hypertrophic scars are especially common in patients who have burns or wounds that heal by secondary intention. These scars, by definition, exceed normal wound healing, causing problems that range from aesthetic deformity to severe limitation of motion. Histologically, these lesions are characterized by randomly distributed tissue bundles consisting of uniaxially oriented extracellular matrix and cells.

In these scars, the over-production and compaction of collagen and proteoglycans [Shetlar, M. R. et al., Burns 4:14 (1977)] exceeds the proliferation of cells. These histological observations suggest that the lesions result from loss of the normal control mechanisms which regulate the synthesis of extracellular matrix during would healing [Shetlar. M. R. et al., Burns 4:14 (1977)]. They are more common on the anterior surfaces of the neck, the shoulder, the chest wall and, in general, the flexor surfaces of the extremities. While some hypertrophic scars will spontaneously resolve within a few years, in many instances, especially in the locations mentioned above, they persist indefinitely. Because these scars are so common, particularly in burns or wounds that heal by secondary intention, their management represents a major unsolved clinical problem.

Keloids are tumors or connective tissue consisting of highly hyperplastic masses which occur in the dermis and adjacent subcutaneous tissue in certain susceptible individuals, most commonly following trauma. Keloid scars are a more severe form of hypertrophic wound scar and form firm dermal nodules of scar which are most commonly preceded by trauma at the site of origin. They are generally larger, grow in an apparently unregulated way, and tend to invade normal tissue surrounding the wound. They are commonly found on the face, earlobes and the medial surface of the ear. The size and growth of these scars often bear little relationship to the magnitude of the skin injury which led to their formation. Keloids often begin as a scratch or an acne pustule, but can grow and become very disfiguring. They rarely resolve spontaneously and often recur even after surgical intervention. Although keloid scars occur in all races, they are more common in African American and Asian populations and in females than in males. The known therapies for keloids have had limited success and they frequently can recur in the site after surgical removal.

The histologic features of disorders of excessive wound healing have been well described. They are characterized by randomly distributed tissue bundles of uniaxially oriented extracellular matrix and cells. Compared to normal scars, the cell density of these scars is low, reflecting the overproduction of collagen and proteoglycans relative to the rate of cell proliferation, which is in conformance with the hypothesis that hypertrophic disorders result from the loss of normal control mechanisms that regulate the synthesis of extracellular matrix during wound healing. Fibroblasts harvested from hypertrophic scars, however, have not been found to be phenotypically abnormal. Hypertrophic scars appear to manifest the influence of epigenetic factors such as mechanical tension on the growth and biosynthetic processes of connective tissue cells. Keloids, on the other hand, result from an abnormal fibroblast phenotype and may therefore be classified as a genetic abnormality.

Scar Formation

Figure 1:
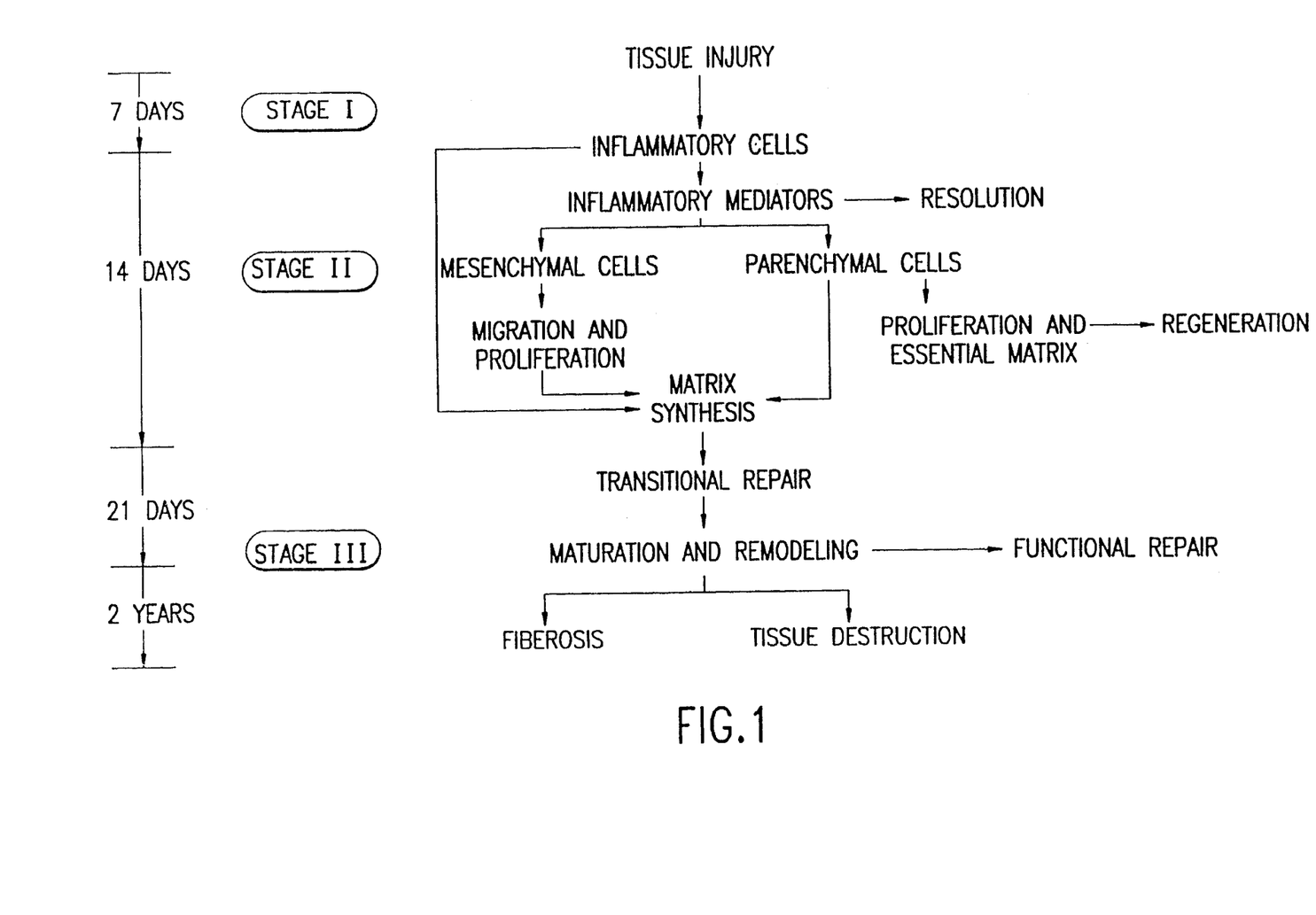
FIG. 1 is a schematic representation of the three-stage process of scar production.

The ability to heal by forming scars is essential for mammalian systems to survive wounding after injury. Normally, wound healing is a continuous process extending over a one-to-two-year period. Conceptually, the wound healing process may be divided into three phases, as illustrated in FIG. 1. The first (stage I) is an intensely degradative phase called the inflammatory stage. It occurs immediately after injury and provides a means to remove the damaged tissues and foreign matter from the wound. This phase lasts approximately one week. Two-to-three days later, as fibroblasts from the surrounding tissue move into the wound, the repairing process enters its second stage (stage II), the proliferation and matrix synthesis stage. The fibroblasts in the wound proliferate and actively produce macromolecules, such as collagen and proteoglycans, which are secreted into the extracellular matrix. The newly-synthesized collagen fibrils are cross-linked by lysyl oxidase and provide structural integrity to the wound. During this stage, fibroblasts also contract the intact collagen in order to reduce the surface area of the wound. This second stage lasts about three weeks. Hypertrophic scars usually appear at this stage.

In the final, remodeling phase (stage III), the previously constructed and randomly organized matrix is remodeled into an organized structure which is highly cross-linked and aligned to maximize mechanical strength. Natural skin wrinkles (relaxed skin tension lines) which align themselves in the direction of mechanical tension and become permanent on the face over time are a common manifestation of this control process. With hypertrophic scars and keloids, the biosynthetic phase continues longer than necessary to repair the wound. In order to maintain nutrient supply in these scars, vascular in-growth occurs, resulting in a large, highly vascularized scar which is unsightly and can be disabling.

Enzyme Action in Collagen Degradation

Enzymes are proteinaceous substances which act as catalysts for biological reactions, in some cases hydrolysis reactions and in others oxidation-reduction processes. Some enzymes have broad activity and others, such as collagenase (Clostridiopeptidase A) produced from the bacterium *Clostridium hystolyticum,* have very specific activity. Highly purified collagenase has been prepared and been found uniquely capable of cleaving bonds in the collagen structure permitting other enzymes to act on the resulting molecular fragments.

The first animal enzyme capable of degrading collagen at neutral pH was isolated from the culture fluid of tadpole tissue. This was shown to cleave the native molecule into two fragments in a highly specific fashion at a temperature below that of denaturation of the substrate. These fragments were characterized by electron microscopy and shown to reflect the cleavage of a native collagen molecule at a specific site closer to the C-terminal end of the molecule, yielding segments of one quarter and three quarters the length of the native collagen molecule; the larger fragment was termed TCA and the smaller fragment TCB.

Figure 2:
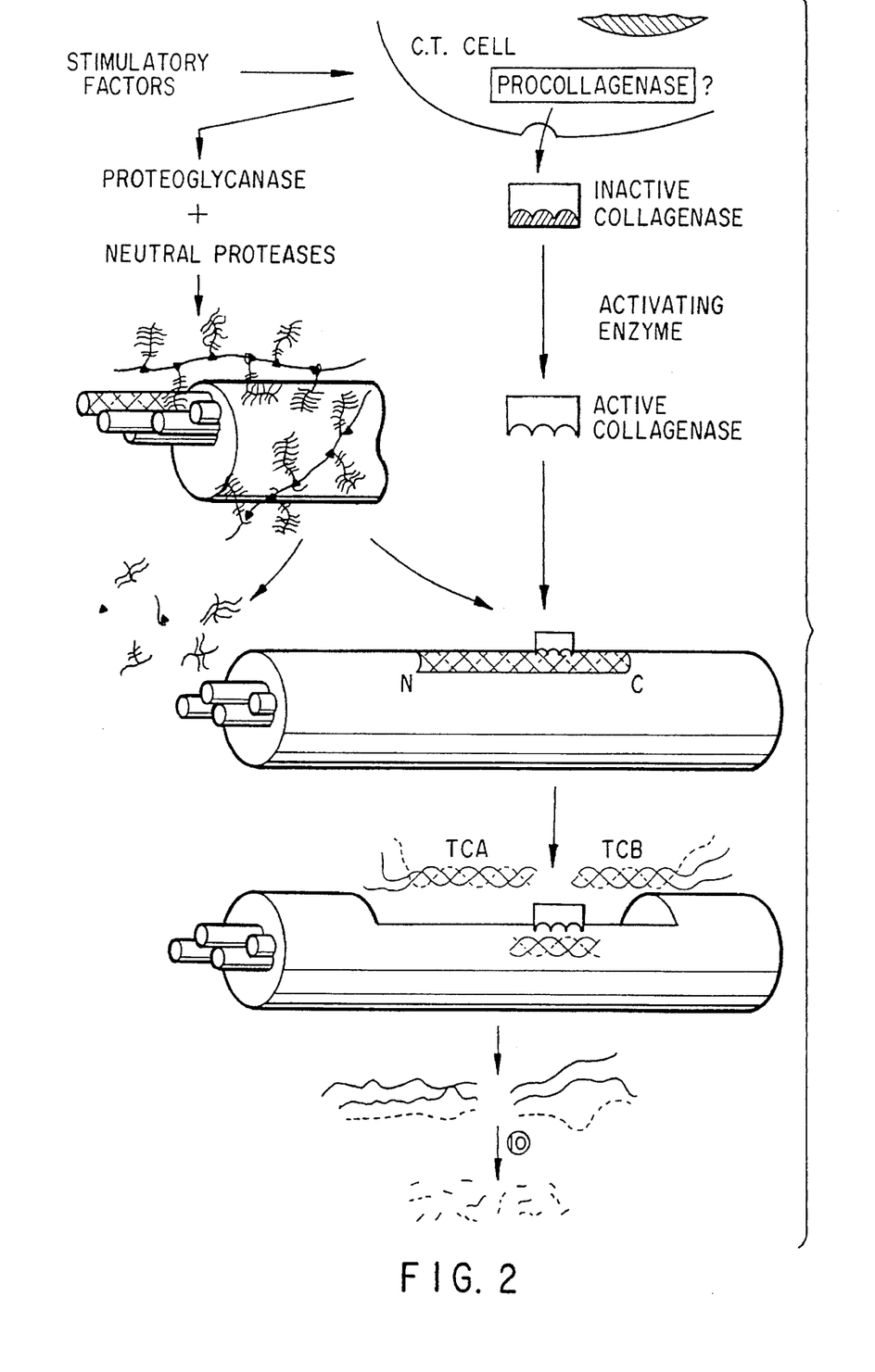
FIG. 2 is a graphic representation of the sequence of events that lead to the degradation of collagen by the enzyme collagenase.

Collagenolytic enzymes have been obtained following cell and organ culture from a wide range of tissues from animal species in which collagen is present. In general, these enzymes have a number of fundamental properties in common; they all have neutral pH optima; they are not stored within the cell, but, rather, appear to be secreted either in an inactive form or bound to inhibitors. FIG. 2 summarizes schematically the fundamental aspects of this enzyme and its mode of action. They appear to be zinc metalloenzymes requiring calcium, and are not inhibited by agents that block serine or sulphydryl-type proteinases. They are inhibited by kelating agents such as EDTA., 1.10-o-phenanthroline, and cysteine, which may inactivate zinc and perhaps other metals required for enzymatic activity and the zinc in the latent enzyme can be replaced by other divalent cations such as Co, Mn, Mg, and Cu. Nearly all the collagenases studied so far have a molecular mass that ranges from 25,000 to 60,000 daltons. The enzymes are usually present in a latent or inactive form. In some instances they seem to be associated with the presence of a zymogen, but in most cases are bound to an inhibitory protein component that can be removed to form the active enzyme; this step is accompanied by a decrease in molecular weight. Although proteolytic enzymes have been mostly used for activation, some latent collagenases can be activated by nonproteolytic agents, such as cheotropic salts or organic mercurial compounds, suggesting that the collagenase and inhibitors, though forming a tight complex, might not be peptide linked as in a proenzyme.

The cells that synthesize collagenase are influenced to a great extent by the environment in which they live. This includes the permanent resident cells of the connective tissues and adjacent structures and the migratory cells that accumulate as a result of injury, inflammation, or immune phenomena, as well as the products secreted by these cells. Epithelial cells and factors secreted by such cells may also play a significant role in the development and remodeling of connective tissues by virtue of their ability to regulate collagenase production by the mesenchymal cells.

Mammalian collagenases display a great deal of specificity by hydrolyzing a single polypeptide bond on each chain of the native triple-stranded collagen helix. A significant amount of work has been devoted to understanding the unique characteristics of the cleavage site. The cleavage site of the $\alpha$-1 chain was identified by electron microscopy and later by sequence analysis.

Although no conclusive physicochemical explanation is available to describe the specificity of the cleavage, there are indications that the helix in that region is thermodynamically less stable. The actual bond cleaved in all species studies is a Gly-Leu or Gly-Ile link. There are slight differences in the amino acid sequence surrounding the scission site; these may account for the differences in the rates at which various collagens are degraded.

The binding of human skin fibroblast collagenase to reconstituted collagen has been recently studied in detail. The enzyme interacts tightly with the collagen fiber and appears to remain bound to the macromolecular aggregate during the degradation process. Approximately 10% of the collagen molecules in the reconstituted collagen appears accessible for binding, in close agreement with the theoretical number of molecules estimated to be present on the surface of the fiber. The in vitro data obtained seemed to indicate that digestion proceeds until completion without the enzyme returning to the solution, but, rather, hopping from one molecule to another. These observations also would explain why collagenase activity is enhanced when the enzyme is exposed to dilute suspensions of re-constituted polymeric collagen rather than compact fibers of large diameter. This mode of action of the enzyme, and its modality of handling the substrate, may explain the low turnover numbers observed (25 molecules of collagen cleaved per enzyme per hour), one of the lowest turnover numbers associated with an enzymatic reaction. It is possible that in vivo the rates could be even slower, due to the presence of enzyme inhibitors and because the active enzyme may have to compete with the latent enzyme for binding sites on the collagen fiber.

Another factor that seems to slow the breakdown of collagen is the presence of cross-links. The introduction of artificial methylene bridges with formaldehyde or of native cross-links by the use of purified lysyl oxidase increases the resistance of collagen to collagenase degradation. Native collagen fibers cross-linked by glutaraldehyde cannot be digested even by bacterial collagenase. Collagen from individuals of increasing age becomes more resistant to enzymatic digestion, suggesting that an age-related accumulation of cross-links may be responsible. It is, therefore, possible that cross-linking of collagen plays a role, not only in generating mechanical stability to the fibers, but also in the regulation of collagen turnover in vivo.

Scar Treatment

Existing therapy for hypertrophic scars and keloids includes surgery, mechanical pressure, steroids, x-ray irradiation and cryotherapy. There are many disadvantages associated with each of these methods. Surgical removal of the scar tissue is often incomplete and can result in the development of hypertrophic scars and keloids at the incision and suture points. Steroid treatments are unpredictable and often result in depigmentation of the skin. X-ray therapy is the only predictably effective treatment to date; however, because of its potential for causing cancer, it is not generally recommended or accepted. The most common approach to control hypertrophic scar and keloid formation is to apply pressure, which appears to be effective in many instances. However, this treatment has limited application, generally based on the size and location of the scar tissue on the body. Other commonly used treatments are application of Vitamin E and corticosteriods. Each of these agents can interfere with collagen synthesis and promote collagen degradation.

An additional method that has been observed empirically to result in general improvement in the appearance and size of treated scars involves covering the scar surface with a wound dressing fabricated from a silicone-based gel [Quinn, K. J., et al., *Burns* 12, 102–108 (1985); Quinn, K. J., *Burns* 13, S33–S40 (1987); Mustoe, T. A., et al., *Surgery* 106, 781–787 (1989).] Quinn et al. used a gel, such as that available from Dow Corning, Arlington, Tex., marketed under the name SILASTIC® gel, and as further described in U.S. Pat. Nos. 4,991,574 assigned to Dow, and 4,838,253 assigned to Johnson & Johnson, herein incorporated by reference.

Silicones are a group of completely synthetic polymers containing the recurring group —$SiR_2O$—, wherein R is a radical such as an alkyl, aryl, phenyl or vinyl group. The simpler silicones are oils of very low melting point, while at the other end of the scale of physical properties are highly cross-linked silicones which form rigid solids. Intermediate in physical properties are silicone elastomers such as gels and rubbers. A variety of such silicone gels have seen used as wound dressings, as disclosed in U.S. Pat. Nos. 4,838,253 to Brassington, and No. 4,991,574 to Pocknell.

Based on experiments involving the measurement of physical parameters associated with the use of such gels, investigators have concluded that the mode of operation of the silicone gel in scar treatment did not involve pressure, temperature, oxygen tension, or occlusion. Rather, as reported, the likely mechanism involved both hydration of the stratum corneum and the release of a low molecular-weight silicone fluid from the gel.

Subsequent investigations by Quinn (1987) and Mustoe, et al. (1989) confirmed the earlier conclusions that neither pressure, temperature, nor oxygen tension could account for the mode of action of the silicone gel in scar treatment, conclusions that remain widely accepted today. Mustoe, et al. (1989) differed from Quinn (1985, 1987) in concluding that a silicone-based chemical interaction was not likely, and in proposing a mechanism based on occlusion of the scar tissue by the silicone gel.

The use of collagenase in medical practice is well known but has heretofore been limited to topical application for debridement of dermal ulcers and burns and, recently, for the treatment of prolapsed intervertebral discs. Purified collagenase has been demonstrated to be relatively safe even in large doses (thousands of units) in animals and in contact with human blood vessels, nerves and bones. U.S. Pat. No. 4,645,668 to Pinnell et al. discloses a method for the treatment of scars involving the injection of a variety of enzymes, some combined with the enzyme collagenase, directly into existing scar tissue. Also disclosed is a method for the prevention of scar formation involving the administration of various enzymes, either alone or in combination, to surgically or traumatically-induced wounds.

Figure 3:
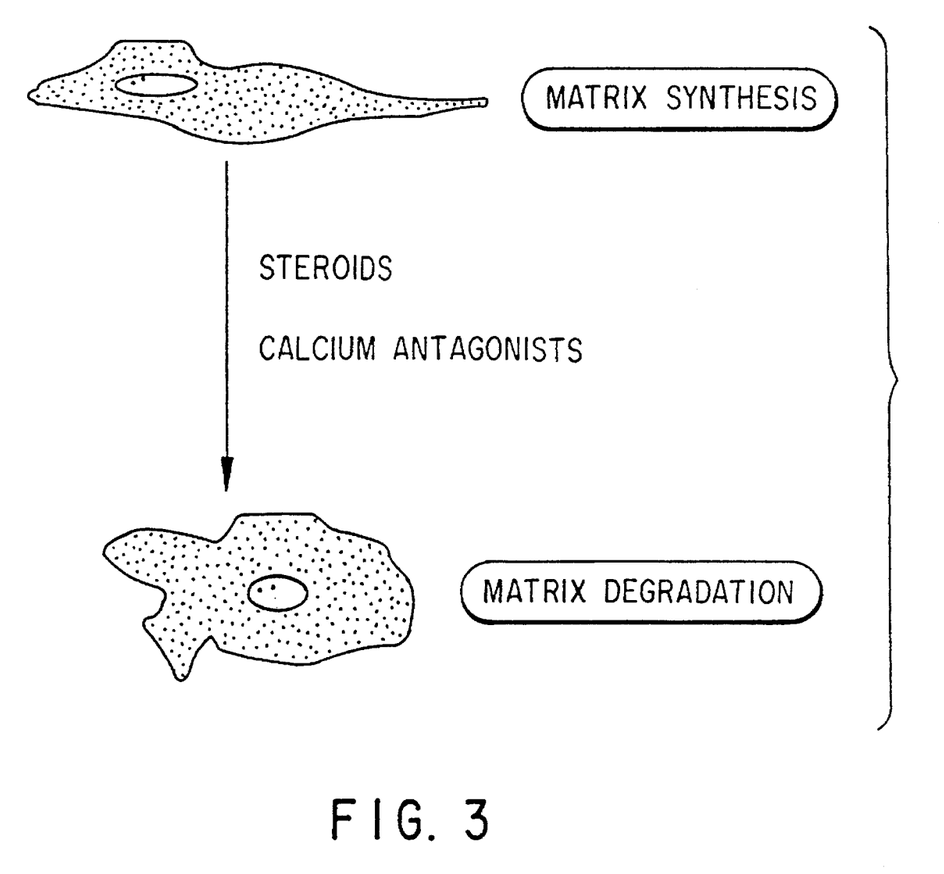
FIG. 3 depicts the changes in collagen cell shape brought about by treatment with calcium antagonists and directly leading to collagen degradation.

U.S. Pat. No. 5,132,119, incorporated herein by reference, has disclosed that calcium antagonists in various forms can drive the cells toward extracellular degradation instead of biosynthesis in the tissue culture environment. Calcium antagonists appear to influence cells to assume a more spherical shape, a result illustrated in FIG. 3. These fibroblasts will concomitantly change their metabolic status from one of synthesis to one of degradation. They also produce considerably more collagenase than the same cell in a more spread configuration, indicating that agents which depolymerize cytocellular proteins inhibit collagen synthesis and accelerate the activity of collagenase. Thus, the factors which control fibroblast shape also control the dynamic balance between extracellular matrix and degradation.

Despite the various treatments presently available, there has been no widely accepted and predictably effective means for preventing or treating hypertrophic scars or keloids.

BRIEF SUMMARY OF THE INVENTION

In one aspect, the present invention provides a method for improving the size and appearance of a scar by stimulating collagenase activity in the scar. In a preferred embodiment, the method of the present invention contemplates improving the size and appearance of scars associated with a fibromatosis, keloid, or a hypertrophic wound healing disorder.

A further aspect of the present invention provides a method for stimulating collagenase activity by covering a scar with a thermal insulating material that elevates the surface temperature of the scar. In a preferred embodiment, the method of the invention stimulates collagenase activity by elevating the surface temperature of the scar from about 0.5° C. to about 5° C. In a more preferred embodiment, the method of the invention stimulates collagenase activity by elevating the surface temperature of the scar from about 1° C. to about 4° C. Still further preferred is a method of the present invention wherein the activity of collagenase is increased by covering the scar with a thermal insulating material that increases the surface temperature of the scar from about 2° C. to about 3° C. In a most preferred embodiment, a thermal material employed in the method of the present invention is a hydrogel.

An additional aspect of the present invention contemplates a method for improving the appearance and size of scars by covering the scar with a thermal insulating material wherein the material contains a therapeutically effective amount of a medicament. In a preferred embodiment, the medicament is a calcium antagonist. More preferably, the calcium antagonist is a calcium inhibitor, a Protein Kinase C inhibitor, or a calcium transport blocker. Preferably, the calcium transport blocker is selected from the group consisting of verapamil, nifedipine, nicardipine, nimodipine, diltiazem, cobalt chloride and nickel chloride. Alternatively, the calcium transport blocker is selected from the group consisting of phenylalkylamine compounds, benzothiazepine compounds and biologically compatible polyvalent salts. Still more preferably, the calmodulin inhibitor is trifluoperazine or tamoxifen.

BRIEF DESCRIPTION OF THE DRAWINGS

In the drawings, which form a part of the specification.

DETAILED DESCRIPTION OF THE INVENTION

In one aspect, the present invention provides a method for improving the size and appearance of a scar by stimulating collagenase activity in the scar. In a preferred embodiment, the method of the present invention contemplates improving the size and appearance of scars associated with a fibromatosis, a keloid, or a hypertrophic wound healing disorder.

The collagenases comprise a class of enzymes distinguished by the ability to initiate the degradation of the native collagen molecule. The existence of such enzymes, as discussed above, has now been recognized in a wide variety of animal species and tissues. The activation energy, $E_A$, of human skin fibroblast collagenase has been measured to be 101,000 calories, a figure greatly exceeding the highest reported values for $E_A$ of other enzymatic reactions. [Eisen, A. Z., et al., J. Bio. Chem. 256, 9516–9521 (1981).] As a consequence, the rates of collagenase reactions are expected to display a high temperature sensitivity, on the order of a thirty-fold increase per 10° C. rise in temperature. [Eisen, A. Z., et al., J. Bio. Chem. 258, 11123–11127 (1981).]

As indicated by the reaction scheme for degradation of collagen as illustrated in FIG. 2, activated collagenase binds to the collagen substrate and proceeds to cleave the collagen molecule into two unequal fragments which then begin to denature (unfolding of helical structure). These fragments are then susceptible to attack by other proteases (enzymes that chemically interact with proteins), resulting in further decomposition of the denatured collagen molecules. Ultimately, nonspecific neutral proteases degrade the collagen polypeptides.

A method of the present invention is thus based upon creating a set of conditions which are effective in bringing about an increase in the activity of the protease enzymes which occur naturally in human fibroblast scar tissue. Based on the kinetics of collagenase reactions as discussed above, a preferred embodiment of the present invention provides a method for stimulating collagenase activity by covering a scar with a thermal insulating material that elevates the surface temperature of the scar. In a preferred embodiment, a method of the invention stimulates collagenase activity by elevating the surface temperature of the scar from about 0.5° C. to about 5° C. In a more preferred embodiment, a method of the invention stimulates collagenase activity by elevating the surface temperature of the scar from about 1° C. to about 4° C. Still further preferred is a method of the present invention wherein the activity of collagenase is increased by covering the scar with a thermal insulating material that increases the surface temperature of the scar from about 2° C. to about 3° C.

An ideal thermal insulating material for use in the present invention is a material that maintains the temperature at the surface of the scar at a value from about 5° to about 5° greater than normal body surface temperature. As is well known in the art, the thermal insulating characteristics of a material result from a balance between the heat capacity of that material and the thermal conductivity of that material. Heat capacity is a measure of the ability of a substance to retain heat. Thermal conductivity is a measure of the capacity of a substance to dissipate heat.

Therefore, it is readily apparent to one of ordinary skill in the art that materials having either a very low heat capacity and a high thermal conductivity, or a very high heat capacity and a low thermal conductivity are inappropriate to the practice of a method of the present invention. Material displaying such an inappropriate balance between these thermal characteristics either fails to maintain scar surface temperature sufficiently above body temperature or, conversely, elevates scar surface temperature well beyond a physiologically appropriate range.

It is readily apparent to one of ordinary skill in the art that there are a variety of materials possessing the appropriate balance of thermal properties suitable for use in the practice of a method of the present invention. However, thermal properties alone cannot serve as the qualifying criteria for selection of an appropriate thermal insulating material for use in the present invention. Such material should also possess a range of mechanical properties suitable for application of the material to a wide variety of locations on the human body. Furthermore, to maximize the desired effect on the size and appearance of scar tissue through the practice of the present invention, it is preferable for the patient to maintain the thermal insulating material in contact with the surface of the scar for extended periods of time. This period of time should preferably be on the order of at least one or more months during which time the material is in thermal contact with the surface of the scar for at least twelve hours, more preferably for at least eighteen hours a day.

A requirement for such extended periods of contact between the thermal insulating material and the scar surface places considerable practical constraints on the mechanical and biological characteristics of an optimal material. The material is preferably relatively light; it is preferably sufficiently flexible to conform to irregular body contours; it preferably possesses sufficient elasticity to adapt to the stresses that accompany the normal range of body movements; and it preferably is not susceptible to generating adverse biological reactions in the tissue with which it is in contact. To facilitate the comfort of the wearer, it should also preferably be capable of repeated removal and reapplication as necessary.

In a most preferred embodiment, the thermal material employed in the method of the present invention is a hydrogel. Hydrogels are three-dimensional networks of hydrophilic polymers, generally covalently or ionically cross-linked, which interact with aqueous solutions by swelling to some equilibrium value. Hydrophilic polymers of which such gels can be composed can be either synthetic or naturally occurring polymers, or combinations of both. The water content of such gels can also vary over a wide range, depending on the chemical identity of the polymers involved, as well as the desired physical characteristics of the resulting composition. Such gels have seen wide use in a number of applications, such as for wound dressings. In this regard, the disclosures of the following U.S. Pat. Nos. are herein incorporated by reference: 5,013,769 to Murray et al; 4,909,244 to Quarfoot et al.; 4,659,700 to Jackson; 4,646,730 to Schonfeld et al; and 3,419,006 to Warwick.

Gels of these types possess desirable thermal and mechanical properties, as well as the necessary biological compatibility. For example, due to the high composition of water in these materials, the heat capacity of these gels is very high, much higher than that for the silicone-based gels, discussed supra, that also see extensive use as wound dressings.

Despite the fact that hydrogels satisfy criteria for a thermal insulating material for use in the method of the present invention, it is recognized by those skilled in the art that there are materials other than hydrogels that possess sufficient characteristics, both thermal and mechanical, to be appropriate for use in the present invention. Without limit, and for illustrative purposes only, these materials can be plaster such as is used typically for the treatment of broken limbs, and pressure bandages such as have seen previous use in methods for the reduction of scar tissue.

An additional aspect of the present invention contemplates a method for improving the appearance and size of scars by covering the scar with a thermal insulating material wherein the material contains a therapeutically effective amount of a medicament. Most preferably, these medicaments can be incorporated into the hydrogel materials disclosed above. Such materials are ideally suited for the incorporation of a wide variety of possible medicaments due to the high water content of the hydrogels. This high water content makes it possible to incorporate virtually any water soluble species therapeutically effective in the treatment of hypertrophic scar tissue or other skin-related conditions. For those therapeutic medicaments that are insoluble in water, one skilled in the appropriate chemical or medicinal arts will recognize that there are various chemical strategies appropriate to the incorporation of hydrophobic species in water-based carriers.

The use of topically applied devices as vehicles for the transdermal delivery of therapeutic agents is well recognized. See, e.g., U.S. Pat. Nos. 5,013,769 to Murray et al.; 4,909,244 to Quarfoot et al.; 4,659,700 to Jackson; 4,646,730 to Schonfeld et al.; and 3,419,006 to Warwick. By incorporation of the teachings of these and other references, it is possible for one skilled in the relevant art to utilize the concepts of transdermal delivery of medicaments in the practice of the present invention.

The present invention thus contemplates a method for improving the appearance and size of scars by covering the scar with a thermal insulating material containing a calcium antagonist. Preferably, the calcium antagonist is a calcium inhibitor, a Protein Kinase C inhibitor, or a calcium transport blocker. Preferably, a calcium transport blocker is verapamil, nifedipine, nicardipine, nimodipine, diltiazem, cobalt chloride or nickel chloride. Alternatively, the calcium transport blocker is a phenylalkylamine compound, a benzothiazepine compound or a biologically compatible polyvalent salt. Still more preferably, the calmodulin inhibitor is trifluoperazine or tamoxifen.

Calcium antagonists, as used herein, are compounds which interfere with calcium transport within a cell or block/inhibit one or more events involved in the calcium cascade. Several classes of calcium antagonists include calmodulin inhibitors, Protein Kinase C inhibitors and calcium transport blockers. Calmodulin inhibitors prevent the binding of calcium to calmodulin, thereby interrupting intracellular signal transduction, including activation of Protein Kinase C, the next event in the calcium cascade. Compounds that inhibit Protein Kinase C or other downstream events can be used. Calmodulin inhibitors include phenothiazines, such as trifluoperazine and tamoxifen (also Protein Kinase C inhibitors). Calcium transport blockers, also called calcium entry antagonists, calcium channel antagonists or calcium channel blockers, block the action of calcium channels, which are regions of cell membranes that facilitate the transport and secretion of fluids and electrolytes such as calcium into the cell [Rasmussen, It. N. E. J. Med. 314: 1094–1101 (1986)]. Compounds included in this class are phenylalkylamine compounds, such as verapamil; polyvalent ionic salts that physically block the calcium channels, such as nickel chloride, cobalt chloride and other biologically acceptable salts of these; hydropyridine compounds, such as nifedipine; and benzothiazepine compounds, such as diltiazem. Other compounds that affect the secondary messenger pathways in cellular signal transduction may have the same or similar effect as calcium antagonists on cell shape and tissue remodeling.

A method of the present invention utilizes the discovery that calcium antagonists, which interfere with calcium metabolism or transport across the cell membrane, can inhibit exocytosis in fibroblast cells; can retard biosynthesis of collagen and sulfated glycosaminoglycans (GAG); can be used to decrease the collagen content of the extracellular matrix; and can also stimulate increased collagenase activity, leading to softening of the scar tissue. These features work together to control wound scar production; by minimizing, preventing or reversing the scarring process, depending upon the course of the disease or type of wound treated.

Exocytosis, a process involved in cellular secretion of protein, is but one mechanism affected by calcium antagonist treatment. During secretion, vesicles that contain sorted and concentrated protein pinch off from the Golgi apparatus and move toward the cell membrane at the leading edge of the cell, where they fuse with the cell membrane and release protein into the extracellular space. This process of fusion and release is known as exocytosis and is one of the essential steps in secretion of extracellular matrix macro-molecules (such as glycosaminoglycans, collagen and elastin). Many diseases and disorders are characterized by excessive biosynthesis or secretion. For example, hypertrophic wound healing disorders are characterized by over-secretion of protein and collagen. This over-production is one factor which contributes to excessive scarring or keloid formation.

Calcium antagonists also regulate cell shape. As described in detail in the Examples, fibroblasts that have been treated with a calcium antagonist became more rounded than untreated fibroblasts. The treated cells were tested for viability and were found to have intact cell membranes which are indicative of viable cells. The observation that treated fibroblast cells become altered was correlated with changes in cell programming from a biosynthetic mode (mechanism normally undertaken by untreated fibroblasts) to a degradative mode. It is believed that this change toward matrix degradation, mediated by cell shape changes, plays a roll in controlling wound scar production. Thus, other compounds can be studied for their ability to regulate (up regulate or down regulate) fibroblast biosynthesis by observing their interaction with calcium antagonists.

In one embodiment, wound scar content can be minimized by incorporating an effective amount of a calcium antagonist into a thermal insulating material, such as a hydrogel, covering a hypertrophic wound site. A scar is covered with a hydrogel containing the calcium antagonist alone, or in combination with a protein synthesis inhibitor (e.g., steroid). Treatment of the wound site by covering with a hydrogel containing the calcium antagonist, with or without the steroid, should continue for a period of time sufficient to minimize the wound area. Suitable calcium antagonists include, but are not limited to phenylalkylamine compounds, such as verapamil; biologically acceptable polyvalent salts, such as cobalt chloride and nickel chloride; hydropyridine compounds, such as nifedipine nicardipine and nimodipine; and phenothiazines, such as trifluoperazine and tamoxifen which are examples of calmodulin inhibitors.

The amount of calcium antagonist which can be effectively administered is dependent upon the type of calcium antagonist used and the scar site to be treated, as well as the nature of the hydrogel or other thermal insulating material used. In an ideal embodiment, the amount is adjusted accordingly depending upon the response observed. Exemplary threshold effective amounts of verapamil and nifedipine are approximately 10 µM and 1 mM, respectively. Steroid which can be used include, but are not limited to; corticosteroids and glucocorticosteroids, such as triamcinolone acetonide (also known as KENALOG™), and Vitamin E (α-tocopherol) (Ehrlich et al. 1972, *Ann. Surg.* 75:235). The amount of steroid which can be effectively administered depends upon the type of steroid used, and the nature of the hydrogel or other thermal insulating material used. The effects of calcium antagonist treatment, with and without steroids, on various types of wound scars are illustrated in the Examples.

Hydropyridine compounds such as nifedipine are relatively insoluble in aqueous solution. Due to their insolubility, it is advantageous to solubilize the drug in a carrier which facilitates its incorporation into a hydrogel.

Depolymerization of cycloskeletal proteins leading to alteration of the cell shape and matrix degradation can be regulated using a methods of this invention. Secondary to this, the invention can be used to regulate and block exocytosis. In particular, fibroblasts are contacted with an effective amount of a calcium antagonist incorporated into a hydrogel or other suitable material, an amount sufficient to degrade the matrix and retard exocytosis to a desired degree.

As will be recognized by one skilled in the appropriate art, practice of the method of the present invention need not be limited to incorporation of the specific medicaments disclosed above.

The following examples illustrate particular embodiments of the present invention and are not limiting of the specification and claims in any way.

EXAMPLE 1

Treatment of Hypertrophic Burn Scars

An adolescent female patient suffering from hypertrophic burn scars was treated by application of a hydrogel wound dressing, NUGEL®, manufactured by Johnson & Johnson Medical Inc., Arlington, Tex. The hydrogel employed was supported by a fusible fiber fabric scrim and protected on both sides by a permeable polyethylene film. No additional medicaments were incorporated in the hydrogel.

Figure 4A:
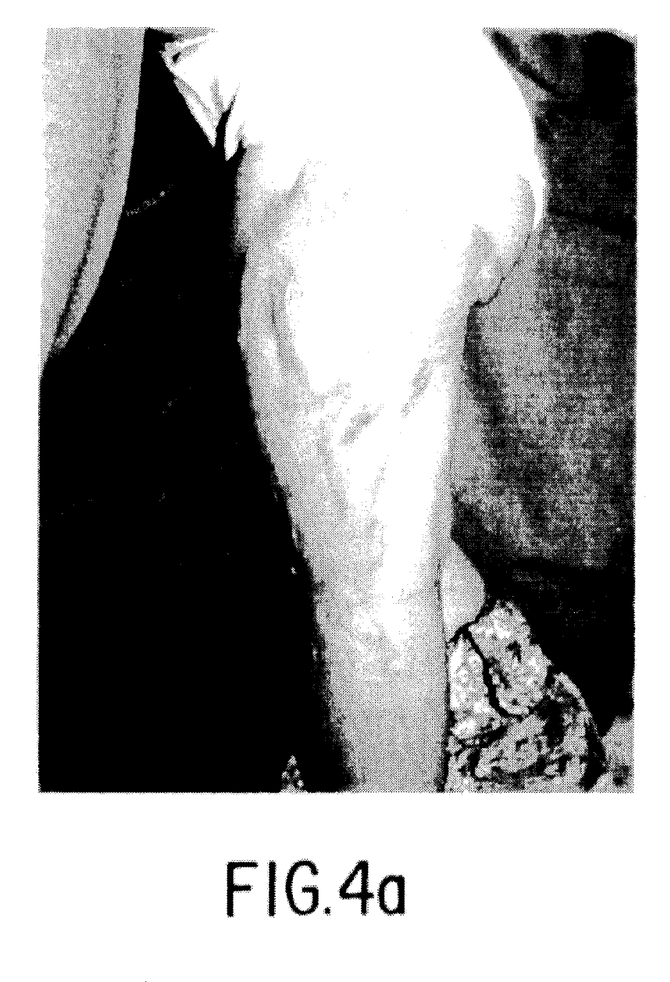
FIG. 4a is a photograph of a hypertrophic burn scar before treatment by a method of the present invention.

As can be seen from FIG. 4a, before treatment the scar possessed all of the physical characteristics typically associated with hypertrophic scars. The scar was significantly elevated from the plane of the surface of the surrounding normal tissue. The scar was further characterized by considerable mass and was highly fibrous in nature. As a consequence of this fibrous nature, and the fact that the scar spans the knee region, considerable reduction in movement of the limb and flexion of the knee resulted. In addition, the color of the scar tissue was considerably different from the surrounding normal tissue, being an "angry," or noticeable, red color.

Figure 4B:
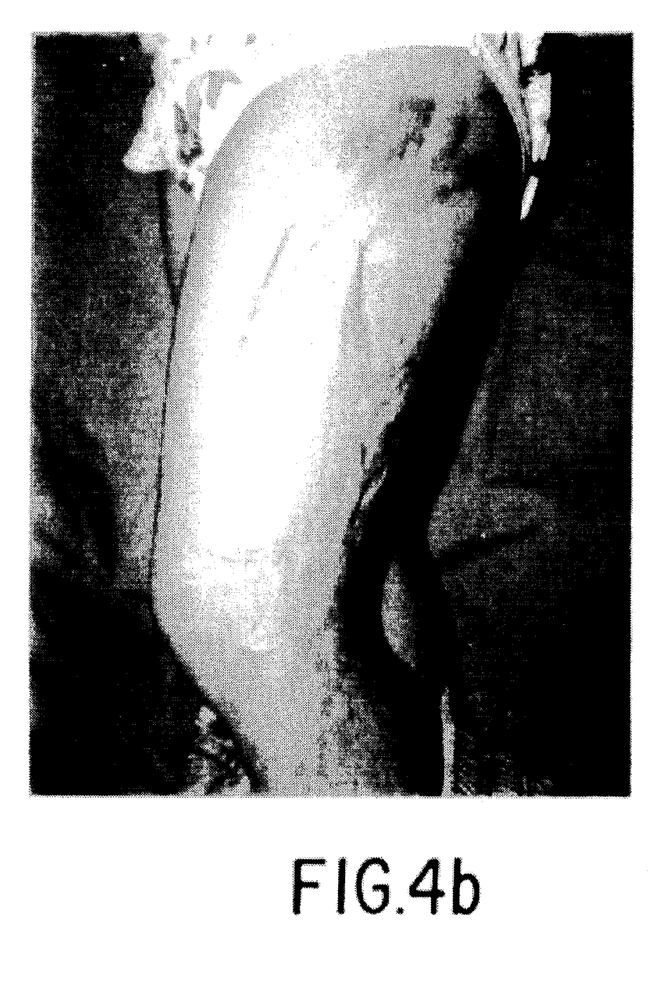
FIG. 4b is a photograph of the hypertrophic burn scar after two months of treatment by a method of the present invention.

FIG. 4b illustrates the same patient following a regime of treatment according to a method of the present invention in which the Johnson & Johnson hydrogel was maintained in contact with the surface of the scar tissue for a period of at least twelve hours a day. This treatment was followed for a period of two months. As FIG. 4b illustrates, the treatment resulted in a considerable improvement in the appearance of the scar. The contrast between the scar and the surrounding normal tissue has been considerably reduced. The total scar volume, as well as the obvious surface fibrosity, have decreased. As a consequence of treatment by the method of the invention, the overall color of the scar faded and now more closely approaches that of the surrounding normal tissue.

The normal recommended course of treatment extends beyond the two month period illustrated in FIG. 4. For optimal results, the treatment regime is continued for at least six months. Results such as these are dependent on the nature and the extent of the scar subject to treatment. In some situations, treatment periods in excess of six months are called for.

EXAMPLE 2

Measurement of Scar Surface Temperature

A hydrogel wound dressing, Gel-Syte™, Baxter Healthcare Corp., Pharmaseal Div., Valencia, Calif., was applied to the surface of a hypertrophic scar. A commercially-available thermocouple device was inserted at the hydrogel/tissue interface. Temperature readings were taken at regular intervals. After an initial period characterized by a slight decrease in surface temperature resulting from contact with the high heat capacity gel, the surface temperature of the scar increased. While the subject remained at rest, surface scar temperature was observed to increase approximately 2°–3° C.

EXAMPLE 3

Studies On Protein And GAG Secretion Tissue Preparation

A connective tissue model of uniaxially oriented cells and extracellular matrix was fabricated using bovine fibroblasts, rat tail tendon collagen and nutrient media. Bovine fascial fibroblasts were harvested from the thigh of freshly slaughtered 2 week old calves (Trelegan's, Cambridge, Mass.) by enzymatic digestion using 0.1% type li collagenase (Worthington Biochemical, Inc., Freehold, N.J.) digestion in Dulbecco's Modified Eagle Medium (DMEM; Gibco, Grand Island, N.Y.) at 37° C. for 4 hours. The released cells were seeded onto tissue culture dishes with DMEM supplemented with 10% NuSerum™ (Collaborative Research, Bedford, Mass.). The media was changed every 48 hours. The cells were passaged once and then either used immediately or stored frozen in 50% calf serum/45% DMEM/5% DMSO at −100° C. When frozen cells were used they were quickly thawed, sedimented through a column of 50% serum/50% DMEM at 185 g for 3 minutes, then plated on coverslips. The media was changed after cell attachment (~4 hours).

Native type I collagen was extracted from rat tail tendon and purified using a modification of the method of Chandrakasan, G. et al., *J. Biol. Chem.* 251: 6062–6067 (1976). Specifically, rat tail tendons were removed from adult Sprague-Dawley rat tails, washed in PBS and distilled water. The tendons were then placed in a solution of 0.05M (3%) acetic acid at the ratio of 200 ml per tail. The mixture was stirred for 96 hours at 8° C.

After 24 hours of stirring, the mixture was filtered through several layers of cheesecloth and then centrifuged at 12000 g (9000 rpm in Sorval GS-3 rotor) for 2 hours. The supernatant was precipitated and redissolved in cold acid multiple times to remove non-collagenous proteins. The collagen solution was sterilized in 1/1000 (v/v) chloroform. This procedure preserves the native structure of the collagen molecule.

Oriented tissue equivalents were made by mixing bovine fibroblasts with a 0.2% collagen solution, 20% calf serum, 10 mg/ml gentamycin solution, 5 mg/ml ascorbate in DMEM as previously described [McLeod, K. J. "Modulation of Biosynthesis by Physiologically Relevant Electric Fields" Ph.D. Thesis M.I.T. 1986]. This suspension was poured into sterile culture dishes containing two sterile porous polyethylene posts held 2 centimeters apart. The dishes were placed in a cell culture incubator gassed at 5% $CO_2$ with 99% humidity. The suspension gelled at 37° C.

Over several days, the fibroblasts remodelled and consolidated the collagen gel around the fixed posts. The resultant oriented fibroblast populated collagen matrix (FPCM) formed a tissue equivalent structure which histologically resembled a ligament. Oriented tissue equivalents are further described in McLeod et al., *Science* 236: 1465–1469 (1987) and in U.S. patent application Ser. No. 07/349,85, filed May 10, 1989, to R. C. Lee and D. Huang, the teachings of which are herein incorporated by reference.

Assay For Determining Biosynthetic Activity

Protein and glycosaminoglycan (GAG) biosynthesis was measured using radiolabeled precursors of protein and sulfated GAGs. Four days after casting of the FPCM, the media bathing the ligament equivalents was changed to serum free DMEM with 5° mM L-proline (Sigma, St. Louis, Mo.). After 12 hours, the media was changed again to fresh serum-free media supplemented with 10 µCi/ml $Na_2^{35}SO_4$ (NEX-041, New England Nuclear, Boston, Mass.), 10 µCi/ml L-[5-$^3$H]-proline (NET-573, New England Nuclear, Boston, Mass.) and 5° mM L-proline. The samples were bathed in the radiolabeled media for 12 hours. The radiolabeled sulfate was incorporated into GAGs and $^3$H-proline into proteins, and so provided markers of sulfated GAGs and protein synthesis, respectively. Since DMEM is proline-free, the addition of non-radioactive proline ensures a relatively constant specific activity in the medium.

Effect Of Calcium Antagonists On Biosynthesis

The effect of calcium antagonists on protein and glycosaminoglycan (GAG) biosynthesis was measured in FPCMs under several conditions. The biosynthetic responses to calcium antagonism were studied in FPCMs cultured n DMEM supplemented with either 5.5 µM glucose or 5.5 µM fructose. Both were studied because energy metabolism of cultured fibroblasts is primarily anaerobic when the carbohydrate energy source is glucose and predominantly aerobic when the carbohydrate source is fructose [Thilly, W. G., *Mammalian Cell Technology*, Chapter 5, Butterworth Publishers, Boston, (1986)]. In vivo fibroblasts are, however, believed to derive their energy primarily through aerobic glycolysis.

The drugs used to antagonize calcium channels were verapamil, nifedipine, cobalt chloride and trifluoperazine. Control studies were performed to test the metabolic state of the cells in the FPCM. The effect of hydroxyurea and antimycin A, a drug which blocks oxidative phosphorylation, on biosynthesis was measured in FPCMs cultured in fructose or glucose.

Results

Energy Metabolism

Figure 5A:
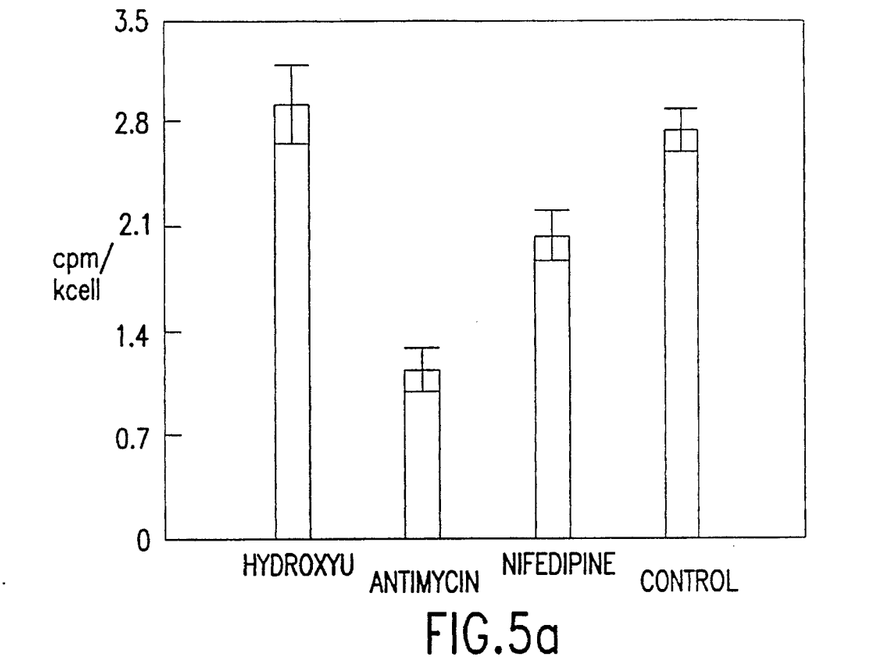
FIG. 5a is a graphic representation of the effects of hydroxyurea (7.9 mM), antimycin A (1.0 µM), and nifedipine (100 µM) on the rate of proline incorporation.
Figure 5B:
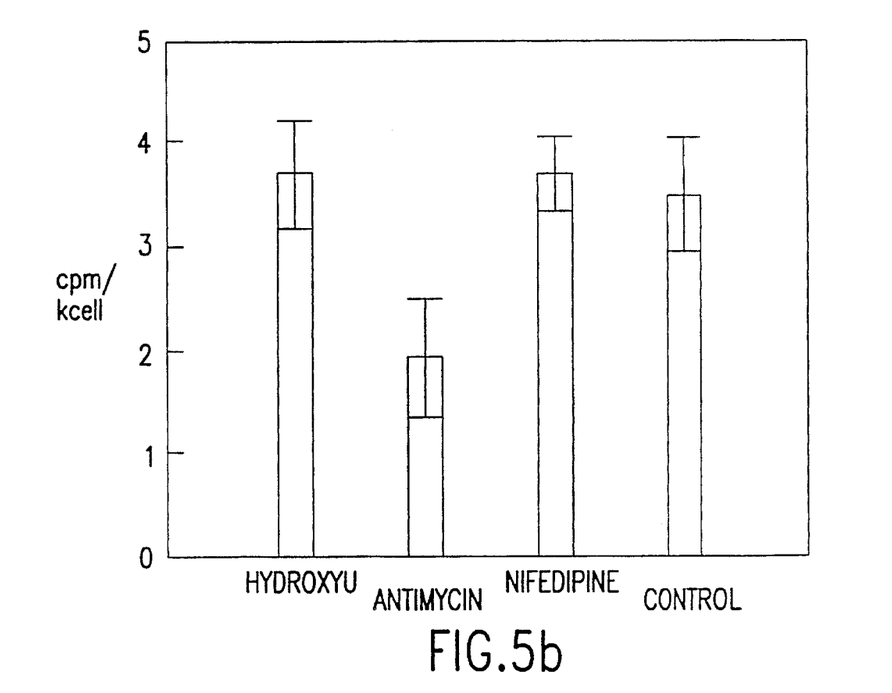
FIG. 5b is a representation of the effect on the rate of sulfate incorporation into fibroblast populated collagen matrices (FPCM) bathed in DMEM/5.5 µM fructose.

As previously reported [Thilly, W. G., *Mammalian Cell Technology*, Chapter 5 Butterworth Publishers, Boston, (1987)], differences between cellular energy metabolism of fibroblasts provided with glucose or fructose as energy substrates were observed. The effects of antimycin A on both incorporation of proline into extracellular matrix protein and incorporation of sulfate into extracellular matrix glycosaminoglycans over a 12 hour period was measured in FPCMs bathed in DMEM/5.5 mM fructose and their results are shown in FIGS. 5a and 5b, respectively. Antimycin A had little effect on $^3$H-proline incorporation with FPCMs provided with glucose. In contrast, antimycin A caused a substantial reduction in the rate of proline incorporation into the extracellular matrix in FPCMs provided with fructose.

Protein and Glycosaminoglycan Biosynthesis

Figure 6A:
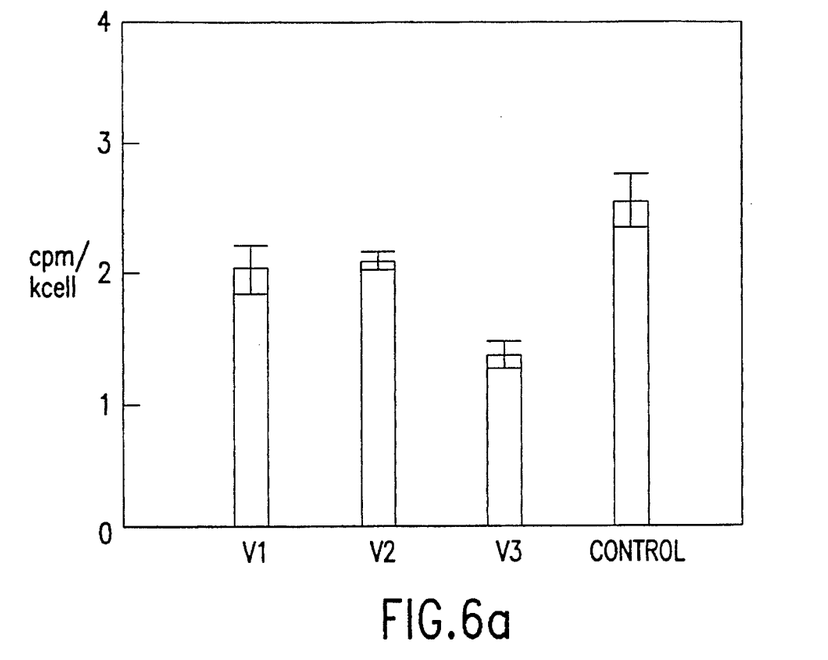
FIG. 6a is a graphic representation of the dose-dependent effect of verapamil on the rate of proline incorporation of FPCM bathed in DMEM/5.5 µM glucose.
Figure 6B:
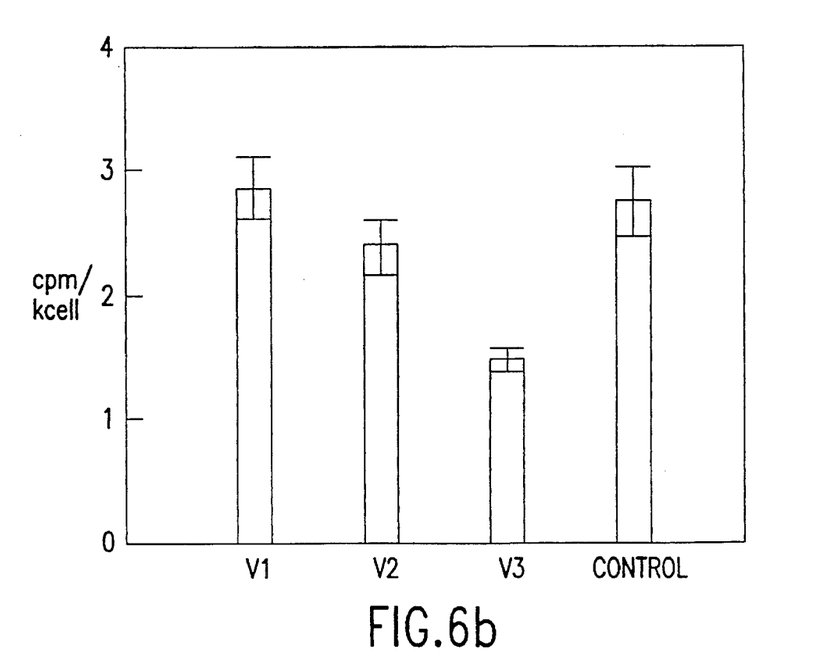
FIG. 6b is a representation of the dose-dependent effect of verapamil on the rate of proline incorporation of FPCM bathed in DMEM/5.5 µM fructose.

When the effect of the carbohydrate source on the rate of biosynthesis of protein and glycosaminoglycan was examined in FPCMs bathed in DMEM/0.5 mM cold proline, no difference was observed between control FPCMs in glucose or fructose (FIG. 6). There was a dose-dependent effect of verapamil on protein incorporation. However, the biosynthetic response to calcium channel blockers was observed to depend on the type of calcium antagonist used and whether the carbohydrate source was glucose or fructose.

Figure 7A:
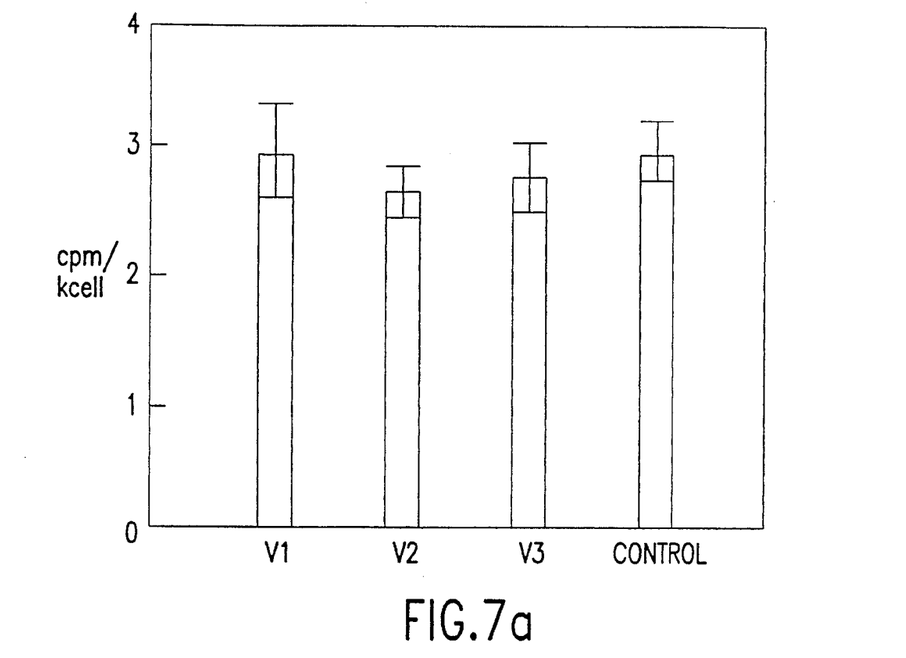
FIG. 7a is a graphic representation of the effects of verapamil on the rate of sulfate incorporation into glycosaminoglycans in FPCM bathed in DMEM/5.5 µm glucose.
Figure 7B:
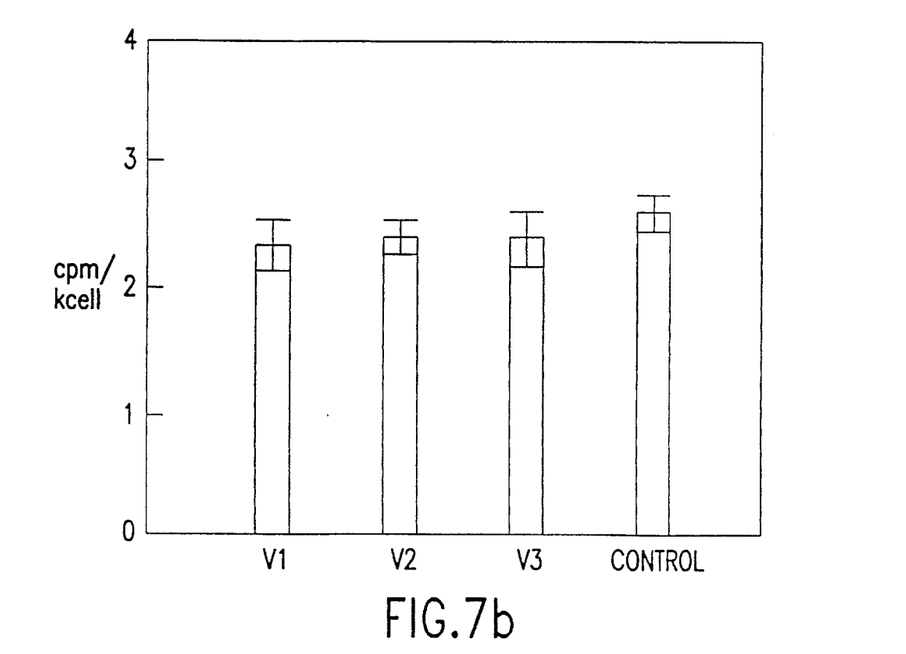
FIG. 7b is a representation of the effects of verapamil on the rate of sulfate incorporation into glycosaminoglycans in FPCM bathed in DMEM/5.5 µM fructose. V1 represents 1 µM verapamil; V2 represents 10 µM verapamil; and V3 represents 100 µM verapamil.

Verapamil retarded the incorporation of $^3$H-proline into the extracellular matrix in the presence of either glucose or fructose (FIG. 6). However, fibroblasts appeared to be more sensitive to verapamil when glucose was used as the metabolic energy source. Verapamil at 100 µM concentration reduced the $^3$H-proline incorporation by almost 50% in FPCMs provided with either glucose or fructose. Verapamil had no significant effect on sulfated glycosaminoglycan biosynthesis, even at a concentration of 100 µM (FIG. 7). The lack of effect on GAG biosynthesis incorporation indicated that the verapamil did not reduce cell viability.

In equimolar concentrations, nifedipine caused a larger reduction of $^3$-proline incorporation than verapamil. As for verapamil, nifedipine at 100 μM concentration had no effect on GAG biosynthesis. When the medium was supplemented with fructose, nifedipine at 10 and 100 μM reduced both proline and sulfate incorporation by 60%. In contrast, nifedipine at 1 μM had no effect on either proline or sulfate incorporation. In a series of 3-week-old FPCMs, twelve hours' incubation in 100 μM nifedipine caused complete digestion of the matrix.

When glucose was used as the carbohydrate source, verapamil at 100 μM concentration was also found to retard the incorporation of $^3$H-proline into the extracellular matrix about 50%. In fact, fibroblasts appeared to be more sensitive to verapamil when glucose was used as the carbohydrate source. The incorporation of $^3$H-proline in the samples treated with 1 and 10 μM verapamil was about 20% less than that of the control. Different concentrations of verapamil also had no effect on sulfated GAG biosynthesis. In summary, it was observed that verapamil an nifedipine at 100 μM each reduced $^3$H-proline incorporation by almost 50-60 in the tissue equivalent.

The rates of $^3$H-proline and sulfated glycosaminoglycan incorporation in fibroblast populated collagen matrices bathed in DMEM/5.5 μM glucose or fructose and a calcium antagonist are shown in Table 1.

50 mg/ml of cobalt chloride had a profound effect in reducing the rate of protein biosynthesis and increasing the rate of secretion of sulfated glycosaminoglycans, as compared with the effects of verapamil.

TABLE I

|  | $^3$H-Froline | Glucose (5.5 μM) Glycosamino-glycans (sulfated) (cpm/1 × $10^3$ cells) | $^3$H-Proline | Fructose (5.5 μM) Glycosam-ino-glycans (sulfated) (cpm/1 × $10^3$) |
| --- | --- | --- | --- | --- |
| Control | 1.00 ± 0.04 (16) | 1.00 ± 0.03 (16) | 1.00 ± 0.05 (16) | 1.00 ± 0.04 (16) |
| Verapami 1 μM) | 0.85 ± 0.02 (16) | 1.02 ± 0.03 (16) | 1.02 ± 0.02 (16) | 1.00 ± 0.04 (16) |
| Cobalt (50 μg/ml) | 0.79 ± 0.01 (16) | 1.14 ± 0.03 (16) | 0.90 ± 0.03 (16) | 1.01 ± 0.02 (16) |

In order to identify whether the decrease in the incorporation of radioisotopes into the matrix was due to the inhibition of cell propagation in the FPCMs, hydroxyurea was used to block DNA synthesis. Hydroxyurea prevents the formation of deoxyribonucleotides. The results showed that there was no effect on hydroxyurea on the $^3$H-proline and $^3$S-sulfate incorporation in either carbohydrate source.

Figure 8:
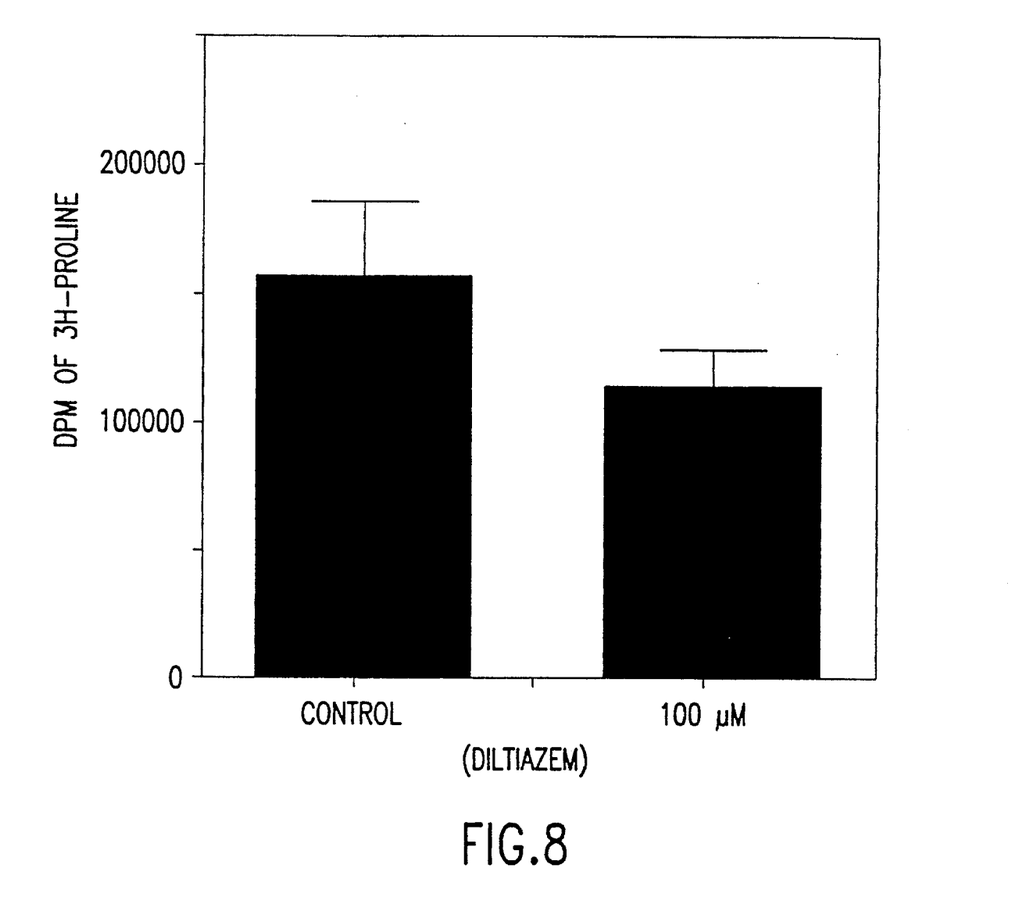
FIG. 8 is a graphic representation of the incorporation of $^3$H-proline into FPCM extracellular matrix. FPCM bathed in fructose were untreated (control) or treated with 100 µM diltiazem.
Figure 9:
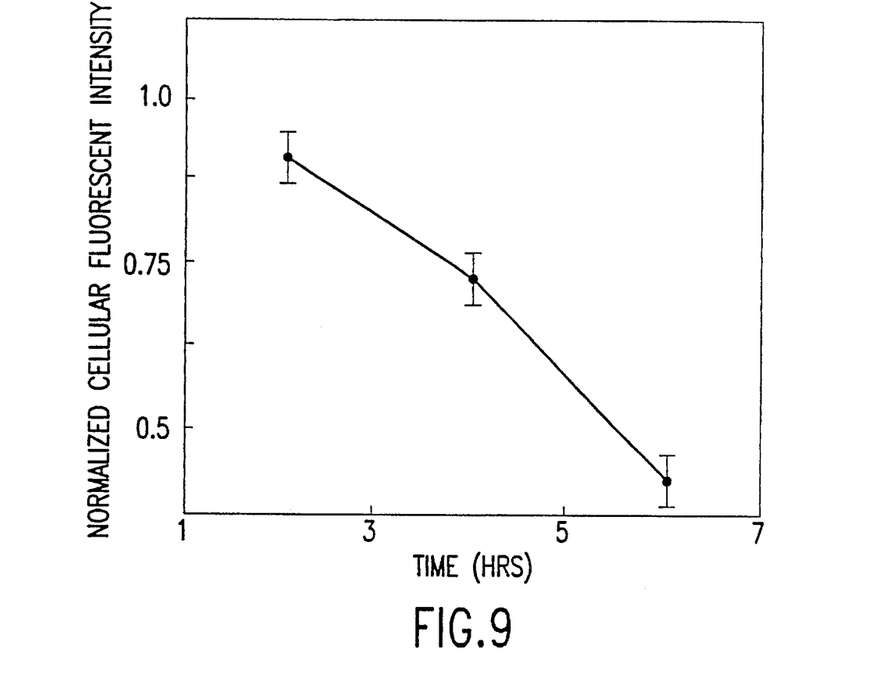
FIG. 9 is graphic representation of the rate of excocytosis in human dermal fibroblasts in monolayer culture as a function of cellular fluorescence versus exposure time. Release of Lucifer Yellow CH from secretory vesicles in fibroblasts into the extracellular space is indicated by cellular fluorescence vs. time after dye loading. Loss of fluorescence occurs via exocytosis. Approximately 55% of the dye is secreted in 6 hours.
Figure 10:
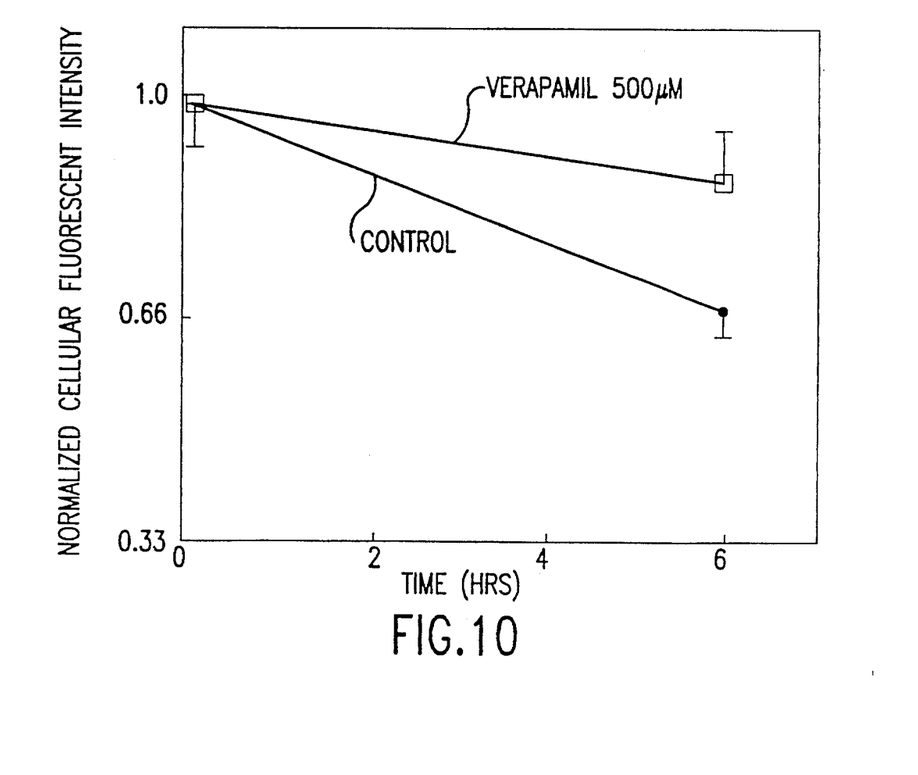
FIG. 10 is a graphic representation of the effect of the calcium antagonist verapamil (50 µM) on release of Lucifer Yellow CH from human dermal fibroblasts in monolayer culture. Retardation of exocytosis is demonstrated.

The effects of other calcium antagonists have been studied. Preliminary data showed that 100 μM ditiazen reduced $^3$H-proline incorporation by about 30% in the connective tissue equivalent. See FIG. 8. Trifluoperazine has also been studied.

EXAMPLE 4

Studies on Exocytosis

Human Fibroblast Cell Culture

Human neonatal foreskin fibroblasts were harvested from newborns at the time of circumcision at the Brigham and Women's Hospital. The samples were initially placed in antibiotic supplemented Dulbecco's Modified Eagles Media (DMEM) then incubated in trypsin for 20 minutes to remove the surface epithelial layer. The tissue was then washed in Phosphate-Buffered Saline (PBS) solution, then centrifuged at 180 g for 5 minutes to separate the epidermal cells. The dermis was minced then subjected to 0.1% type II collagenase (Worthington Biochemical Inc., Freehold, N.J.) digestion in DMEM for 4 hours. The released cells were seeded onto tissue culture dishes with DMEM supplemented with 10% NuSerum™ (Collaborative Research, Bedford, Mass.). The media was changed every 48 hours. The cells were passed once and then were either used immediately or stored frozen in 50% serum/45% DMSO at-100° C. When frozen cells were used they were quickly thawed, sedimented through a column of 50% serum/50% DMEM at 185 g for 3 minutes, then plated on coverslips. The media was changed after cell attachment (~4 hours).

Quantification of Dye Release

To determine if the rate of fluid phase exocytosis was modulated by calcium antagonists, the rate of exocytosis in human fibroblasts was measured using the rate of release of Lucifer yellow labeled dextran (LYD, M. W. 10,000) (Molecular Probes Inc., Portland, Oreg.), from vesicles in the cytoplasm of human foreskin fibroblasts. The LYD was loaded into cells by fluid phase pinocytosis (endocytosis) in the absence of serum. The intracellular location and transport of the dye was monitored under control and experimental conditions using video image analysis.

$P_2$-$P_5$ fibroblast cells were harvested from monolayer by brief Ix trypsin and ethylenediaminetetraacetic acid (EDTA) digestion, plated on glass coverslips and allowed to become 50% confluent. Cell laden coverslips (CLCS) were bathed in DMEM supplemented with 5 mg/ml Lucifer Yellow CH Dextran (LYD) for 12 hours under standard conditions. The CLSC were then washed five times in PBS at 37° C. to remove extracellular LYD, then placed in 60 mm sterile cell culture dishes. The dishes contained serum free DMEM at 37° C. supplemented with either verapamil (10 μM), or no drug (control). The dishes were returned from each of the dishes after 0, 2, 4 and 6 hours. They were quickly immersed in neutral buffered formalin at 8° C. allowed 20 minutes to fix, then the CLCS were mounted on glass microscope slides. The mounting solution was 50% glycerol, NaF phenylaminediamine.

Each cell to be analyzed was placed in the center position within the field of view. The LY fluorescence was excited by filtered 100 watt mercury arc lamp illumination. The excitation was filtered with an interference filter with a bandpass of 460–485 nm. The emission was collected with a 40x objective and passed through a 515 nm barrier filter. The emission was recorded with a video camera head with a chalnicon tube, digitized and stored by a Hamamatus video image processor under the control of a VaxStation II computer. This procedure was repeated under phase illumination so that the boundaries of the cell could be accurately identified by phase contrast. A software program located the boundaries of the cell by identifying pixels with intensity values more than two standard deviations below the mean background pixel intensity in a manually chosen background area.

To quantify the average intensity in the cell cytoplasm, the mean background value ($b_m$) was subtracted from the entire image including the pixel values in the cell ($P_i$). Since the background intensity could be used as a measure of the excitation intensity, the net pixel values within the boundaries of the cell were normalized to $B_m$. To normalized pixel values were then summed, and that sum was normalized to the area of the cell (A). This result was termed the intensity of the cell $I_o$:

$I_c=\Sigma_i(P_i-B_m)/B_mA$ $I_c$ was determined for each of the 50 cells, 25 from each of two simultaneously-removed coverslips. The standard deviation and means were then calculated. The mean for two coverslips was plotted at each time point (2, 4 and 6 hours). This process was carried out for both the experimentals and controls at each time point.

Results

Exocytosis

Exocytosis was observed to proceed at a near constant rate over a six hour period of observation in human dermal fibroblasts in monolayer culture (FIG. 7b). The rate of exocytosis of Lucifer yellow dextran was found to be sensitive to plasma membrane calcium channel function. Both verapamil (10 μM) and nifedipine (100 μM) were found to significantly retard exocytosis over a six hour period in these cells (FIG. 6, Tables II and III). These results clearly demonstrate that exocytosis in human fibroblasts can be regulated. In FIG. 7b, the controls are represented by the squares. Table II and III show the retardation of exocytosis in human dermal fibroblasts by calcium channel blockers, verapamil (50 μM) and nifedipine (1 μM), respectively.

TABLE II

Effect Of Verapamil On Exocytosis Response

| Stimulus | Exposure Time Hours | Average Intensity | Standard Error | Intensity Difference | p Value |
|---|---|---|---|---|---|
| Control | 0 | 855 | 38 | | |
|  | 6 | 691 | 23 | | |
| Verapamil 50 μM | 6 | 793 | 35 | 14.8 % | p < 0.02 |

TABLE III

Effect Of Nifedipine On Exocytosis Response

| Stimulus | Exposure Time (Hours) | Average Normalized Intensity | Standard Error | p Value |
|---|---|---|---|---|
| Control | 0 | .58 | .029 | |
|  | 4 | .54 | .029 | |
|  | 6 | .36 | .015 | |
| Nifedipine: 1 μM | 4 | .58 | .029 | p > 0.05 |
|  | 6 | .49 | .047 | p < 0.03 |

EXAMPLE 5

Study On Cell Shape Changes Caused By Calcium Antagonists

Light and electron microscopy studies indicated that verapamil caused the cells to adopt a more rounded shape than controls. These rounded cells were tested for viability by staining the cells with 0.01% trypan blue for 5 minutes. Most of the cells were not stained with trypan blue indicating that the cell membranes were intact and cells remain viable. Again, alteration of cell shape correlates with the change in cell programming from biosynthetic mode to a degradative mode. Based upon this observation, it is hypothesized that calcium channel blockers drive the cells toward matrix degradation, perhaps mediated by cell shape changes.

EXAMPLE 6

Studies Of The Effect Of Verapamil In Conjunction With A Glucocorticoid On Human Keloid And Hypertrophic Scars The first patients to be tested were those patients with intractable keloids scars that had failed to respond to multiple therapeutic trails with glucocortoids (Kenalog™). In order to determine if verapamil can induce breakdown of the scar matrix and produce macroscopic shrinkage and softening of the scar, three patients were given 1 mM verapamil in one lesion and 1 mM lidocaine in a similar lesion in the same or contralateral area of the body.

The response to the initial injection of verapamil was dramatic softening of the scars. The lidocaine did not produce softening of the scars. On subsequent injection of verapamil at biweekly intervals, the response of keloid scars was to return gradually towards the original stiffness of the scar. However, in patients with hypertrophic scars, the response to verapamil therapy was equally effective on the first injection, but these scars differed from keloid scars. in that further injection led to further softening and fading of the scars, Dramatic results have occurred in patents with burn scar contractures. In two patients injected with verapamil alone, the scar contracture disappeared in two-to-three weeks. Results for other diagnoses were also positive. One patient with a hypertrophic scar on the volar surface of the wrist received verapamil injections into the scar site, causing a 10–30 reduction in the scar size and rapid fading of the scar. Another with hypertrophic scars on the right wrist and knee experienced rapid fading and shrinkage of scars with verapamil injections. Verapamil injections into a scar contracture of the joints on the hand of another individual allowed a substantial increase in range of motion by 15–20 degrees, and decreased hard edema. A patient whose left hand and right palm were affected by Dupuytren's disease experienced softening of the areas after one verapamil injection; finger extension was also increased by 10 degrees.

All references cited herein are incorporated by reference to the extent that they supplement, explain, provide a background for, or teach methodology, techniques, and/or compositions employed herein.

What is claimed is:

1. A method for improving the size and appearance of an existing hypertrophic or keloid scar comprising stimulating collagenase activity in said scar for a period of time sufficient to result in a noticeable improvement in said scar, wherein stimulating collagenase activity is accomplished by covering said scar with a thermal insulating material that elevates the surface temperature of the scar from about 0.5° C. to about 5° C., wherein said thermal insulating material contains a therapeutically effective amount of a medicament.

2. The method of claim 1 wherein the medicament is a calcium antagonist.

3. The method of claim 2 wherein the calcium antagonist is a calmodulin inhibitor, a Protein Kinase C inhibitor, or a calcium transport blocker.

4. The method of claim 3 wherein the calcium transport blocker is verapamil, nifedipine, nicardipine, nimodipine, diltiazem, cobalt chloride or nickel chloride.

5. The method of claim 3 wherein the calcium transport blocker is a phenylalkylamine compound, a benzothiazepine compound, or a biologically compatible polyvalent salts.

6. The method of claim 3 wherein the calmodulin inhibitor is trifluoperazine or tamoxifen.

7. A method for improving the size and appearance of a hypertrophic or keloid scar comprising covering said scar with a hydrogel-containing composition for a period of time sufficient to reduce the amount of scar tissue, thereby resulting in a noticeable improvement in said scar after removal of said hydrogel-containing composition.

8. The method according to claim 7 wherein said hydrogel-containing composition comprises a therapeutically effective amount of a medicament.

9. The method of claim 8 wherein the medicament is a calcium antagonist.

10. The method of claim 9 wherein the calcium antagonist is a calmodulin inhibitor, a Protein Kinase C inhibitor, or a calcium transport blocker.

11. The method of claim 10 wherein the calcium transport blocker is verapamil, nifedipine, nicardipine, nimodipine, diltiazem, cobalt chloride or nickel chloride.

12. The method of claim 10 wherein the calcium transport blocker is a phenylalkylamine compound, a benzothiazepine compound, or a biologically compatible polyvalent salts.

13. The method of claim 10 wherein the calmodulin inhibitor is trifluoperazine or tamoxifen.

* * * * *